United States Patent
Warnqvist et al.

(10) Patent No.: US 10,160,706 B2
(45) Date of Patent: Dec. 25, 2018

(54) PROCESS FOR REMOVAL OF SULPHUR FROM RAW METHANOL

(71) Applicant: ANDRITZ OY, Helsinki (FI)

(72) Inventors: Jan Warnqvist, Vikbolandet (SE); Johan Olsson Släger, Svedala (SE); Anders Eliasson, Mörrum (SE)

(73) Assignee: ANDRITZ OY, Helsinki (FI)

( * ) Notice: Subject to any disclaimer, the term of this patent is extended or adjusted under 35 U.S.C. 154(b) by 188 days.

(21) Appl. No.: 15/027,967

(22) PCT Filed: Oct. 13, 2014

(86) PCT No.: PCT/SE2014/051205
§ 371 (c)(1),
(2) Date: Apr. 7, 2016

(87) PCT Pub. No.: WO2015/053704
PCT Pub. Date: Apr. 16, 2015

(65) Prior Publication Data
US 2016/0237011 A1    Aug. 18, 2016

(30) Foreign Application Priority Data
Oct. 11, 2013 (SE) ........................ 1351209

(51) Int. Cl.
*C07C 29/86* (2006.01)
*C07C 29/80* (2006.01)
*C07C 29/88* (2006.01)
*B01D 3/14* (2006.01)
*B01D 11/04* (2006.01)
*D21C 11/00* (2006.01)

(52) U.S. Cl.
CPC .............. *C07C 29/86* (2013.01); *B01D 3/143* (2013.01); *B01D 11/0488* (2013.01); *B01D 11/0492* (2013.01); *C07C 29/80* (2013.01); *C07C 29/88* (2013.01); *D21C 11/0007* (2013.01)

(58) Field of Classification Search
CPC ......... C07C 29/74; C07C 29/76; C07C 29/86; B01D 11/04; B01D 12/00
See application file for complete search history.

(56) References Cited

U.S. PATENT DOCUMENTS 4,961,918 A    10/1990    Norell et al.
5,450,892 A    9/1995    Gautreaux et al.
(Continued)

FOREIGN PATENT DOCUMENTS

CA    1088957        11/1980
CN    202398144 U    8/2012
(Continued)

OTHER PUBLICATIONS

Anna Von Schenck et al., "Cleaning Methanol for Transportation Use," Skogsindistriella Programmet, Report 1076, Värmeforsk Service AB, Dec. 2008, Stockholm, SE.
(Continued)

*Primary Examiner* — Brian A McCaig
(74) *Attorney, Agent, or Firm* — Honigman Miller Schwartz and Cohn LLP; Anna M. Budde (57) ABSTRACT

A method for purifying raw methanol containing sulfur compounds, wherein the method comprises the step of washing raw methanol with a non-polar organic solvent.

18 Claims, 3 Drawing Sheets

(56) References Cited

U.S. PATENT DOCUMENTS 5,718,810 A * 2/1998 Robbins ................. B01D 3/146
                                                              203/76
8,440,159 B2    5/2013 Brucher et al.

FOREIGN PATENT DOCUMENTS

| EP | 0430699 A2 | 11/1990 |
|----|------------|---------|
| FI | 52710 | 8/1977 |
| JP | S63135342 A | 6/1988 |
| JP | 2005089347 A | 4/2005 |
| SE | 430411 | 10/1977 |
| SU | 56125 | 11/1939 |
| WO | 2009/059920 A2 | 5/2009 |
| WO | 2009070110 | 6/2009 |
| WO | 2010091492 A1 | 8/2010 |
| WO | 2012104491 | 8/2012 |
| WO | 2013067287 A1 | 5/2013 |
| WO | 2014/201555 A1 | 12/2014 |

OTHER PUBLICATIONS

PCT International Search Report and Written Opinion for Application No. PCT/SE2014/051205, dated Feb. 2, 2015.
Svensson, Sara, "Minimizing the Sulphur Content in Kraft Lignin," Degree Project, ECTS 30.0 at STFI-Packforsk, Stockholm, 2008.
Office Action/Search Report for Russian Application No. 2016112932/04(020337) dated Jun. 7, 2018.
English Translation of Search Report for JP 2016-521949, dated Sep. 25, 2018.

* cited by examiner

PROCESS FOR REMOVAL OF SULPHUR FROM RAW METHANOL

This application is a 35 USC § 371 United States national stage application of International Application No. PCT/SE2014/051205, filed Oct. 13, 2014, which is incorporated herein by reference in its entirety, and which claims priority to Swedish Patent Application No. 1351209-0, filed Oct. 11, 2013.

TECHNICAL FIELD

The present invention relates to a method of purifying raw methanol. More particularly this invention relates to the removal of impurities including sulfurous compounds from raw methanol obtained as a by-product in the kraft or sulfate process of pulp production in pulp mills.

BACKGROUND

Methanol is a simple alcohol which is used as a reagent in many manufacturing processes and as a fuel.

The demand for green sources of methanol has increased recently, due in part to increasing prices of other energy sources, a demand for non-fossil fuels and a demand for methanol as a component in other processes. This increase in demand has lead to a renewed interest in the purification of raw methanol.

During the kraft or sulfate process of pulp production in pulp mills, methanol is obtained as a by-product. The obtained raw methanol is contaminated with impurities, such as sulfurous organic compounds, ethanol, ammonia, as well as turpentine (mixture of various terpenes). Kraft pulping consists of the digestion of wood chips at high temperature and pressure in diluted alkaline liquor containing sodium hydroxide and sodium sulfide as active ingredients. The digestion disrupts the cellular structure and causes the dissolution of lignin, other chemical products contained in the wood and hemi-cellulose. Thus, the cellulose fiber dispersed in the spent liquor from the digestion may be isolated by filtration. The reaming liquor, known as black liquor, is further evaporated and calcinated for the recovery of salts and alkalis, which return to the kraft pulping process.

Raw methanol is obtained during the process by the demethylation of methoxyl groups found mainly on the lignin polymer. Raw methanol is primarily obtained in the condensates from the evaporation of the black liquor. However, raw methanol is also obtained at other points in the pulping process, such as in condensates and vapors from the digestion phase.

During pulp production from pine and spruce around 6 kg of raw methanol is obtained per tonne of pulp (theoretically up to about 9.5 kg could be obtained). The methanol is obtained in the condensates from black liquor evaporation and condensates from the digestion system and enriched by distillation. The methanol content in this enriched stream is typically fairly high (>75 wt. %) although being contaminated. It is further possible to extract more methanol than 6 kg per tonne as there are more sub-processes in a pulp mill where a cleavage of methyl groups results in the formation of methanol, such as oxygen bleaching/bleaching/evaporation. However, this is not performed today as the raw methanol has little to no economic value.

The 6 kg or more of raw methanol could be considered a small amount of energy from an energy usage perspective but it is indirectly important as it is a green methanol with an effective carbon footprint of 0.

The primary reason that the raw methanol is not used in other processes is that it is usually deemed impossible to transport off site due primarily to odor problems, as the raw methanol is contaminated with sulfurous compounds, e.g. $H_2S$, methyl mercaptan, dimethyl sulfide, but also less volatile sulfurous compounds. When other dangers are considered, such as high $H_2S$ concentrations and toxicity, basically all pulp mills have opted to destroy the methanol by combustion using completely closed systems directly after the extraction of methanol from the evaporation system.

There are existing processes for purifying raw methanol. Such a process is described in FI52710 by Suokas for Kemi OY. In the disclosed process a stream of raw methanol is first acidified causing the precipitation of ammonium salts, subsequently the raw methanol is distilled, whereby any volatile sulfurous compounds, e.g. $H_2S$, methyl mercaptan, and dimethyl sulfide, are removed while methanol remains in the bottom fraction. The raw methanol is then treated with an oxidizing agent to increase the boiling point of any remaining dissolved sulfurous compounds. Subsequently, methanol is separated from the water phase, comprising high boiling, oxidized sulfurous compounds, by distillation or steam stripping to provide methanol with a low content of sulfurous compounds.

U.S. Pat. No. 8,440,159 to Metso Power AB relates to a similar process as the one disclosed in FI52710. In the Metso process the acidified raw methanol mixture is heated whilst maintaining a concentration of ammonium salts below the concentration at which they precipitate. The raw methanol is evaporated from the acidified mixture and subsequently treated as in FI52710.

Both these processes require a significant amount of chemical reagents, e.g. oxidating agents, which are costly to both procure and dispose of. They furthermore require extensive capital construction costs.

The relatively low volume available at each production facility combined with the relatively high construction and reagent costs implies that it is unprofitable to install any of the existing technology solutions. Accordingly, methanol is still just burned of at the pulp mill to generate heat.

Nor is there any possibility to transport raw methanol to a central processing facility to achieve economies of scale. Such a system would need to be designed to process the entire Scandinavian region's overall volume of raw methanol to produce enough methanol, to account for the construction costs for such a plant.

As a result of the unprofitability of installing existing purification systems, it is still deemed to be more cost-effective to simply burn the methanol.

More efficient methods of purification are thus required for it to be possible to purify raw methanol in a cost-effective manner, whereby green methanol for production of e.g. methyl esters of fatty acids of plant origin (FAME), i.e. biodiesel, could be produced as a by-product in pulp production.

SUMMARY

The present invention seeks to mitigate, alleviate, circumvent or eliminate at least one, such as one or more, of the above-identified deficiencies of the art.

Accordingly there is, according to one aspect of the invention, provided a method for purifying raw methanol containing sulfurous compounds. The method comprises the step of washing raw methanol with a non-polar organic solvent.

According to an aspect of the invention, the non-polar organic solvent:
- has a boiling point higher than 100° C., such as higher than 150° C., 200° C., 250° C., or 300° C.;
- is a solvent comprising at least 60 wt. %, such as at least 70, 75, 80, 85, or 90 wt. %, alkanes and/or cyclo-alkanes having a carbon number of 14 or higher;
- comprises less than 2.5 wt. % polycyclic aromatic hydrocarbons;
- has a viscosity at 40° C. of not more than 100 cSt, such as not more than 75 cSt, 50 cSt, or 25 cSt;
- is a mixture of hydrocarbons, e.g. mineral oil, white oil, mineral oil, paraffin oil, or any mixture thereof; and/or
- has a density at 25° C. in the range 0.80 to 0.90 g/cm$^3$, such as in the range 0.82 to 0.88 or 0.83 to 0.87 g/cm$^3$ g/cm$^3$; or in the range 0.91 to 1.20 g/cm$^3$.

According to an aspect of the invention, the method further comprises the step of diluting the raw methanol with water before being washed with the non-polar organic solvent; the methanol content in the raw methanol before being diluted preferably being at least 65 wt. %, such as 80 to 90 wt. %. Subsequent to the dilution, turpentine may be separated before washing the diluted aqueous methanol with the non-polar organic solvent.

According to an aspect of the invention, the non-polar organic solvent is regenerated, such as by steam stripping, and re-used.

According to an aspect of the invention, the raw methanol is acidified, such as by adding sulfuric acid, and precipitated salts are removed before washing the raw methanol with a non-polar organic solvent. Subsequent to the acidification, the methanol may be distilled. The distillation may be performed in a manner such that volatile contaminants, such as sulfurous compounds, firstly are distilled of and then methanol.

According to an aspect of the invention, the content of water, acetone, and/or ethanol in the washed methanol is reduced by distillation after the wash with the non-polar organic solvent.

Further advantageous features of the invention are defined in the dependent claims. In addition, advantageous features of the invention are elaborated in embodiments disclosed herein.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DETAILED DESCRIPTION

In order to be able to use the raw methanol from pulp production in e.g. production of FAME, it must be purified and the level of contaminants reduced. A purification process must however be cost effective, such that the price attainable for the methanol exceeds the cost of purification.

In the art, raw methanol has typically been purified using a distillation and chemical processes, such as those disclosed by Metso (cf. U.S. Pat. No. 8,440,159) and Kemi OY (cf. FI52710). These processes are however not suitable for production of methanol at a cost level suitable for industrial use, e.g. production of biodiesel.

As already described, raw methanol is typically obtained as a by-product in kraft pulping. The present invention relates to a cost effective process for removal of sulfurous compounds and optionally other contaminants, e.g. ammonia and turpentine, as well from raw methanol. The process comprises washing the raw methanol with a non-polar organic solvent, whereby extracting sulfurous compounds and other contaminants from the methanol. The low cost method of the process makes it economically viable to treat raw methanol directly at a pulp mill, or to treat methanol from several pulp mills, such that the methanol obtained can be used in further processes. The washing process can be incorporated into the existing kraft pulping process. Further, the process can also be incorporated in to existing methods for raw methanol purification to improve their efficiency.

Thus, an embodiment relates to method for purifying raw methanol containing sulfurous compounds, comprising washing the raw methanol with a non-polar organic solvent. Typically, the raw methanol, besides sulfurous compounds, also comprises water, ammonia and turpentine. Most of the contaminants present in the raw methanol, especially sulfurous compounds, are relatively insoluble in polar solvents, such as methanol. Such contaminants are however far more soluble in less polar solvents. The present inventors have shown that washing raw methanol with a non-polar organic solvent effectively and efficiently extracts sulfurous contaminants. Further, also remaining residues of turpentine may be removed. The major part of turpentine is however more efficiently removed by phase separation (may require dilution with water) followed be decantation. Washing raw methanol with a non-polar organic solvent thus provides methanol with a significantly lowered amount of sulfurous contaminants in a cost efficient manner; especially as the non-polar organic solvent may be regenerated and re-used.

Raw methanol obtained in pulping processes is typically has a fairly high methanol content, such as at least 65 wt. %, and typically 80 to 90 wt. %, as it commonly is obtained as a distillate in enriching various condensates comprising methanol by distillation.

In order to increase the hydrophilicity, and whereby facilitate phase separation during the washing, the water content may be increased before the extraction by adding water. Further, increasing the water content will also increase the density of the methanol phase, which, for a lighter solvent, also will contribute to facilitating phase separation during the washing. Furthermore, addition of water may assist in separating turpentine, which may be decanted before washing the methanol. Thus, water is, according to an embodiment, added to the methanol before the wash a non-polar organic solvent.

According to an embodiment, the water content is adjusted in a manner such that the methanol phase obtains higher density than the non-polar organic solvent used. As outlined below, washing aqueous methanol having higher density than the non-polar organic solvent used in the washing may reduce the content of non-polar solvent in the washed methanol.

In embodiments, wherein a heavier solvent, such as a solvent having a density at 25° C. of more than 0.91 g/ml, is used, the water content may be increased in a manner such that the methanol phase still has lower density than the non-polar organic solvent used. In such embodiments, the density of the diluted aqueous methanol after the addition of water may be less than 0.90 g/ml at 25° C., e.g. 0.82 to 0.89 g/ml or 0.85 to 0.87 g/ml at 25° C.

The density of aqueous methanol is proportional to water content. According to an embodiment, water is added to adjust the density at 25° C. to 0.87 to 0.91 g/ml such as, to 0.88 to 0.90 g/ml. Thus, the water may be added to adjust the density at 25° C. to about 0.89 g/ml. The density may be determined in accordance with ASTM E 346-D 891.

According to another embodiment, the water is added to adjust the density of the diluted aqueous methanol at 25° C. to 0.82 to 0.91, such as to 0.83 to 0.89 g/ml or to 0.85 to 0.87 g/ml. Lower water content implies that removal of water by distillation requires less energy.

According to an embodiment, the water content of the aqueous methanol and the non-polar organic solvent are selected in manner such that difference in density at 25° C. is at least 0.01 g/ml, such as at least 0.02, 0.025, 0.03, or 0.05 g/ml.

Not only the methanol content of the aqueous methanol, but also the properties of the non-polar organic solvent may be of importance. In order to obtain phase separation in washing the methanol, the non-polar organic solvent should not be miscible, or miscible to very low degree, with aqueous methanol. Preferably, the methanol should dissolve less than 1 g of the non-polar organic solvent, such as less than 0.5 or less than 0.1 g of the non-polar organic solvent, per 100 g methanol. Not only the water content of the methanol, but also the lipophilicity of non-polar organic solvent will determine the amount of non-polar organic solvent that may be dissolved in the methanol. Further, the non-polar organic solvent should preferable have high boiling point to facilitate regeneration by steam treatment. The non-polar organic solvent should preferable also be fairly inert towards contaminants and methanol at temperatures up to about 60° C.

According to an embodiment, the non-polar organic solvent comprises alkanes and/or cyclo-alkanes, such as at least 50, 60, 70, 80, or 90 wt. %, alkanes and/or cyclo-alkanes. The alkanes and/or cyclo-alkanes may be C8 to C20 alkanes and cyclo-alkanes, such as C12 to C16 alkanes and/or cyclo-alkanes. Further, the non-polar organic solvent may comprise at least 50 wt % C8 to C20 alkanes and/or C8 to C20 cyclo-alkanes. In an embodiment, wherein the non-polar organic solvent comprises C8 to C20 alkanes and/or C8 to C20 cyclo-alkanes, it may comprise at least 60 wt. %, such as at least 70, 75, 80, 85, or 90 wt. %, C8 to C20 alkanes and/or C8 to C20 cyclo-alkanes.

In embodiments, wherein the non-polar organic solvent is to be regenerated, it preferably has a boiling point higher than 100° C., such as higher than 150° C., 200° C., 250° C. or even higher than 300° C. A high boiling point, i.e. at least 100° C. implies that the non-polar organic solvent may be regenerated by steam stripping and subsequently re-used.

Further, non-polar organic solvents comprising mixtures of hydrocarbons, representing a preferred type of non-polar organic solvent, typically displays a boiling point interval. The lower end for the boiling point interval may be higher than 100° C., such as higher than 150° C., 200° C., 250° C., or even higher than 300° C. Further, the upper end for the boiling point interval may be less than 600° C., such as less than 560° C.

In non-polar organic solvent comprising alkanes and/or cyclo-alkanes, the carbon number of the alkanes and/or cyclo-alkanes, i.e. their number of carbon atoms, will correlate to the boiling point of the solvent. As an example n-hexadecane has a boiling point of about 287° C., while n-tetradecane has a boiling point of about 254° C. The carbon number for the major part of alkanes and/or cyclo-alkanes in non-polar organic solvent having a boiling point of about at least 250° C. will thus be 14 or greater.

According to an embodiment, the non-polar organic solvent, is a solvent comprising at least 60 wt. %, such as at least 70, 75, 80, 85, or 90 wt. %, alkanes and/or cyclo-alkanes having a carbon number of 14 or higher. Preferably, the content of polycyclic aromatic hydrocarbons is less than 2.5 wt. %, such as less than 1.0 wt. %. Further, the non-polar organic solvent may comprise less than 10 wt. %, such as less than 15 wt. %, alkanes and/or cyclo-alkanes having a carbon number of 30 or higher.

Further, the degree of higher alkanes and cyclo-alkanes will not only affect the boiling properties, but also viscosity of the non-polar organic solvent.

A too highly viscous non-polar organic solvent may be harder to process. Thus, the non-polar organic solvent, according to an embodiment, has a viscosity at 40° C. of not more than 100 cSt, such as not more than 75 cSt, 50 cSt or 25 cSt. Further, the non-polar organic solvent is preferably liquid at 40° C., such as at 30° C., 20° C., or 10° C. The density of non-organic polar given herein is, according to an embodiment, determined in accordance with ASTM D-445.

Examples of non-polar organic solvents comprising alkanes and cyclo-alkanes suitable for use in the present washing of methanol are hexadecane, white mineral oils, white oils, mineral oils, and paraffin oils. Mineral oils or paraffin oils can comprise a mixture of naphthenic and paraffinic oils. For embodiments, wherein the non-polar organic solvent are white mineral oils, white oils, mineral oils, or paraffin oils, the above provided guidance with respect to boiling points and density are applicable.

According to an embodiment, the non-polar organic solvent is a white mineral oil, a white oil, a mineral oil, or a paraffin oil:

having a viscosity at 40° C. of not more than 100 cSt, such as not more than 75 cSt, 50 cSt or 25 cSt at 40° C.;

having a boiling point of at least 100° C., such as at least 150° C., 200° C., 250° C. or at least 300° C.; and/or having a content of polycyclic aromatic hydrocarbons of less than 2.5 wt. %, such as less than 1.0 wt. %.

According to another embodiment, the non-polar organic solvent is a mixture of hydrocarbons:

having a viscosity at 40° C. of not more than 100 cSt, such as not more than 75 cSt, 50 cSt or 25 cSt at 40° C.;

having a boiling point of at least 100° C., such as at least 150° C., 200° C., 250° C. or at least 300° C.; and/or having a content of polycyclic aromatic hydrocarbons of up to 10 wt. %.

Further, not only the density of the aqueous methanol to be washed but also the density of the non-polar organic solvent may be of importance. According to an embodiment, the density at 25° C. of the non-polar organic solvent thus is in the range 0.80 to 0.90 g/cm$^3$, such as 0.82 to 0.88 g/cm$^3$ or 0.83 to 0.87 g/cm$^3$. However, the non-polar organic solvent may also be a denser non-polar organic solvent, having a density at 25° C. of at least 0.91 g/cm$^3$, such as 0.91 to 1.20 g/cm$^3$ or 0.91 to 1.0 g/cm$^3$. Mixtures of hydrocarbons comprising aromatic hydrocarbons are typically denser than mixtures with no or low content of aromatic hydrocarbons.

Further, examples of non-polar organic solvent that may be used in washing methanol comprising sulfurous contaminants are triglycerides, which are liquid at temperatures of less than 50° C., such at temperatures of less than 40, 30, or 20° C. As an example, the non-polar organic solvent may be palm oil.

According to an embodiment, the non-polar organic solvent comprises triglycerides, such as at least 10 wt. %, such as at least 25, 50, 75, 85, or 90 wt. %, triglycerides.

Ideally the non-polar organic solvent has a low level of unsaturated hydrocarbons and/or triglycerides. For example, the non-polar organic solvent can have an iodine value of less than approximately 55 measured according to the Wijs Method of measuring iodine value.

Washing the raw methanol with the non-polar organic solvent may be performed batch wise or continuously. If performed batch wise, the washing may repeated one or several times.

In performing the washing the, the methanol to non-polar organic solvent ratio may vary. As an example, the volume ratio may be 1:0.75 to 1:5, the volume of methanol including water and other contaminants.

The sulfurous compounds are believed to be dissolved and extracted more efficiently if the non-polar organic solvent makes up the continuous phase and raw methanol the disperse phase during the washing. Preferably, slight excess of the non-polar organic solvent is thus used in the washing step. According, to an embodiment the non-polar organic solvent to methanol volume ratio is from 1.01:1 to 1.5:1, such as 1.1:1 to 1.3:1, e.g. about 1.2:1, in the washing.

The washing process can occur in a vessel adapted to receive a stream of raw methanol to be washed and a stream of non-polar organic solvent. The vessel may be a vertically aligned column. The column may be modified to increase the contact area between the non-polar organic solvent and the raw methanol, such as by inducing turbulence, i.e. mixing of the methanol and the non-polar organic solvent. Further, the column should preferably also have sections with less turbulence, to allow for the two phases being transported in opposite directions.

In one embodiment, a vertically aligned column may thus comprise perforated plate(s). Typically, such a column has a series of perforated plates or trays arranged axially along the column. For example, the column can comprise several plates provided with holes. The diameter of the holes may be 5 to 15 mm, such as around 10 mm. The plates can be formed such that less than 50% of the cross sectional area of is perforated. For example, the plates can be formed such that between 50% and 30% of the plate area cross sectional area is perforated.

In another embodiment vertically aligned column can be filled with packing bodies, such as glass beads, such that the contact surface between raw methanol and the non-polar organic solvent is increased. Further, also columns with stirring may be used. Such columns may have stirring arranged along the vertical axis.

Columns with perforated trays may be less prone to be negatively affected by fouling compared to a column with packing bodies. Further, it may be easier to clean a column with perforated trays than a column with packing bodies.

Further, the washing may be performed in one or several vessel(s) with stirring. Such a vessel is more suited for batch wise washing, than for continuous. Several communicating vessels with stirring, such as mixer-settler vessels, arranged horizontal, beside each other, may also be used in continuous washing.

In an embodiment, wherein a vertically aligned column is used for the washing, the methanol is fed into the upper or lower part of the column, such as an area approximately at one end of the column, the non-polar organic solvent being fed to the other. The liquid, i.e. methanol or the non-polar organic solvent, having higher density is fed to the upper part of the column. The other liquid, having lower density is fed to the lower part of the column.

As outlined above, it may be preferred to perform the washing with a non-polar organic solvent having lower density than the methanol. The density of the methanol may be increased bay adding water. Washing denser aqueous methanol, moving downwards in the washing column, counter the flow of the non-polar organic solvent, was found to result in less non-polar organic solvent in the methanol.

In a column being provided with a series of perforated plates or trays arranged axially along the column, one of the liquids is provided between the uppermost and second-uppermost plate, the other being provided between bottommost and second-bottommost plate. Thus, the methanol and the non-polar organic solvent traverse the extraction vessel in opposing directions. The raw methanol and the non-polar organic solvent form a dispersion within the column, whereby sulfurous contaminants originally present in the methanol are dissolved in the non-polar organic solvent. At one of the ends of the column, a washed layer of washed methanol is formed. At the other, a layer of non-polar organic solvent comprising sulfurous contaminants is formed. The layer of washed methanol can be tapped, preferably continuously, from the column. Similarly, the non-polar organic solvent can be tapped, preferably continuously, from the column. The tapped non-polar organic solvent may be discarded or regenerated. If regenerated non-polar organic solvent is used for further washing, some fresh non-polar organic solvent may be added as a make up.

In comparison with existing methods such as Suokas, the oxidation step can be replaced by a washing process with regenerated non-polar organic solvent thus saving both energy and chemicals, thus reducing the cost for purifying raw methanol significantly.

In a multi-cycle washing process the washing step is repeated several times and the non-polar organic solvent is regenerated between washing cycles.

The washing may be performed at a temperature of 15 to 60° C., such as at temperature of 40 to 55° C. Performing the wash at elevated temperature implies that the non-polar organic solvent is less viscous, which facilitates the washing. The temperature may be elevated by heating the non-polar organic solvent prior to the wash. In steam re-generating the non-polar organic solvent, the temperature of the non-polar organic solvent will inherently be increased and it may even be necessary to lower its temperature before being re-introduced into the washing step.

As stated above the non-polar organic solvent can be regenerated. A preferred way of regenerating the non-polar organic solvent is stripping with steam (steam blowing).

Stripping transfers sulfurous contaminants from the liquid phase of the non-polar organic solvent into a gas phase. Further, also terpenes (i.e. turpentine) may by stripped of, if present. Small amounts of sulfurous contaminants may remain in the non-polar organic solvent after regeneration. Seemingly, some sulfurous contaminants are irreversible bound to the non-polar organic solvent. However, is was shown that not all sulfurous contaminants have to be removed in order for the non-polar organic solvent to be effectively regenerated for further use in washing raw methanol. Eventually, the non-polar organic solvent may need to be discarded and replaced.

In the stripping process for regeneration of the non-polar organic solvent containing sulfurous contaminants, the non-polar organic solvent may be fed into a stripping vessel. The stripping vessel can be a packed column, spray tower, bubble column or centrifugal contactors or any other suitable stripping vessel. The non-polar organic solvent is stripped with steam.

In an embodiment the stripping vessel is a column provided with perforated plates or trays displaced regularly along the length of the column. Alternatively, the column may comprise filling bodies. Typically, the column is vertically arranged. The non-polar organic solvent may be introduced at the upper end of the column and taken out at the lower, while the steam is introduced in the lower end and taken out at the upper. This provides for efficient stripping of the non-polar organic solvent.

In stripping the non-polar organic solvent, steam is then fed in to the stripping vessel and brought into contact with non-polar organic solvent. The steam can be fed in at a ratio of around between 0.1 to 1 kg steam to 1 kg non-polar organic solvent, for example 0.3 to 0.6 kg steam to 1 kg non-polar organic solvent, such as about 0.45 kg steam to 1 kg non-polar organic solvent. The amount of steam used can be higher or lower depending on the non-polar organic solvent used, type of stripping vessel and factors such as the quantity of sulfur and/or terpenes in the non-polar organic solvent.

Typically, the stripped non-polar organic solvent is re-fed to the washing vessel. Before being re-fed to the washing vessel, the washed non-polar organic solvent is heat-exchanged with the non-polar organic solvent to be regenerated. The temperature of non-polar organic solvent used in washing the methanol should preferably not exceed the boiling point of the methanol. According to an embodiment, the temperature of non-polar organic solvent used in washing the methanol is not more than 60° C. Further, the temperature of non-polar organic solvent used in washing the methanol may be at least 40° C.

The steam containing the sulfurous contaminants can be fed from the vessel via a condenser. The condensate containing sulfur formed at this condenser can be drained to a waste system. The uncondensed gases can be routed to the plant's rich gas system.

The non-polar organic solvent can be steam stripped in a continuous process or batch-wise process. According to an embodiment, the stripping is a continuous process.

As stated above, raw methanol, obtained via evaporation of black liquor in the kraft pulping, comprises various more or less volatile contaminants, such as hydrogen sulfide, methyl mercaptan, dimethyl sulfide, dimethyl disulfide among other sulfurous compounds. Prior to washing the methanol with the non-polar organic solvent, the amounts of sulfurous compounds more volatile than methanol, e.g. hydrogen sulfide, methyl mercaptan, and dimethyl sulfide, may be reduced. Such volatile sulfurous compounds may be removed by condensing gaseous raw methanol at temperature only slightly below its boiling point. Further, they may be distilled of from liquid raw methanol.

Furthermore, liquid raw methanol comprising volatile sulfurous compounds may be distilled in order to increase relative content of methanol and decrease the relative content of water and/or turpentine. Further, volatile sulfurous compounds may be distilled off before distilling methanol. If operated in a batch wise manner, volatile sulfurous compounds may be distilled off before distilling off methanol. This may be performed by adjusting the heating, the reflux from the condenser and cooling of the condenser. In continuous process, two columns, or a partition column, may used to distill of volatile sulfurous compounds separate from distilling methanol.

Apart from sulfurous compounds, the raw methanol also typically comprises nitrogenous compounds, mainly ammonia, and turpentine. In order to remove ammonia, and other nitrogenous compounds, the raw methanol may be acidified. Ammonium salts having low solubility will form in the raw methanol upon acidification, whereby they will precipitate and may be removed.

According to an embodiment, the raw methanol is acidified and precipitated salts removed. Precipitated salts may removed by conventional techniques, such as decantation and/or filtration. Acidification will further facilitate subsequent evaporation of remaining volatile sulfurous compounds, being slightly acidic (e.g. hydrogen sulfide and methyl mercaptan), as their solubility in a raw methanol ceases more or less upon acidification.

The acidification and removal of precipitated salts is typically performed before washing the raw methanol with a non-polar organic solvent. As will be discussed further below, the raw methanol may be distilled subsequent to the acidification. The distillation typically takes place before the wash with the non-polar organic solvent.

In order to precipitate ammonium salts and facilitating the subsequent evaporation of remaining slightly acidic volatile sulfurous compounds, the pH should be 4.5 or lower. By adding acid, the pH may be set to between 2 and 4.5, such as to between 2 and 3 or 4.0 and 4.5. The higher pH interval may be advantageous in embodiments, wherein the methanol content is to be maintained as high as possible in this step.

According to an embodiment, sulfuric acid is added to the raw methanol to lower the pH. As sulfurous compounds anyhow are present in the raw methanol, the use of sulfuric acid avoids introducing further types of contaminants in the methanol.

The pH of the raw methanol can be measured directly, or indirectly by measuring the conductivity, whilst acid is added to ensure that the desired pH is achieved. A bulk amount of acid can also be added without measuring the pH. The ratio of acid to raw methanol should be sufficient that the desired pH is achieved in the raw methanol.

Acidification of the volatile sulfurous compounds is an improvement over stripping as disclosed by Kemi OY, as stripping produces substantial quantities of gas that can not be handled in existing pulp mill systems for elimination of gaseous sulfurous emissions. This implies in such cases that the gases must be scrubbed with a strong alkaline liquid, such as white liquor, to clean process air. Any aspect of this would lead to increased gaseous sulfurous emissions and an increase in "smell" from the factory. Both aspects are undesirable. When stripping is replaced by acidification, a very concentrated gas is generated which meets the requirements for connection to a pulp mill rich gas system. This simplifies both the process of methanol treatment and disposal of the stripped sulfurous compounds.

Turpentine may separate during the acidification. To avoid the generation of a distinct layer of turpentine the raw methanol can be stirred or agitated. This agitation also eases the ability of any gases to escape the raw methanol mixture.

Turpentine may removed by decantation from the raw methanol subsequent to the acidification. By adding water, phase separation may be facilitated and turpentine more effectively removed. Thus, water is added according to an embodiment. The water content may be increased by adding water and/or using a diluted acid in the acidification.

However, high water content will imply that more heat is required in the evaporation step subsequent to the acidification. It may thus be advantageous to avoid diluting the methanol at this stage of the process. Further, diluting the methanol will imply that more salts are dissolved in the methanol and thus not precipitated. According to an embodiment, the water content is increased by less than one unit of percentage (weight) in the acidification step.

To separate the raw methanol from the acid and non-precipitated ammonium salts the methanol may be evaporated, e.g. by distillation. An evaporation step will also remove any volatile sulfurous compounds remaining.

According to an embodiment, the methanol is distilled subsequently to having been acidified; preferably in a manner such that volatile contaminants, such as sulfurous compounds, firstly are distilled of and then methanol. The distillation may be batch wise or continuous. In a continuous process, it may be necessary to include two steps to allow for firstly distilling of volatile contaminants, such as sulfurous compounds. Two continuous distillation steps may be performed in two separate columns or in a partition column.

In an embodiment, wherein the distillation is performed batch wise, the distillation may be performed in such a manner that sulfurous compounds firstly are distilled of, before methanol is distilled of. The distillation may comprise a condensing or chilling step to better control the temperature of the heated gases. Initially the condensing may be performed in manner such that any evaporated methanol is condensed while, evaporated sulfurous compounds are not. Further, the temperature of the methanol to be distilled may gradually be increased.

In an embodiment, wherein the distillation is performed continuously, it may include two steps, wherein volatile contaminants, such as sulfurous compounds, are distilled of in a first step and the methanol in a second step.

In an embodiment, wherein the distillation is continuous the cooling of the overhead product may be adjusted such that methanol, but not all volatile sulfurous compounds, are condensed. The gaseous sulfurous compounds may be vented to the rich-gas system at the pulping mill.

As already discussed, the methanol may be diluted with water prior to washing with the non-polar organic solvent. Diluting the methanol has the advantages of facilitating separation of any remaining turpentine and improving the separation of the non-polar organic solvent and methanol during the washing step.

According to an embodiment, the methanol is diluted with water prior to washing with the non-polar organic solvent, as already described. Further, turpentine may be removed, such as be decantation, after the methanol has diluted but before being washed.

As an example, the raw methanol can be held in buffer tanks prior to washing with non-polar organic solvent. Before being washed, water may be added. Turpentine separated upon addition of water may be separated, such as by decanting in a decanter, before the washing step. Depending on the density of the aqueous methanol, the turpentine phase may be lighter or denser than methanol phase.

Turpentine forming a layer at the top or bottom of the buffer tank can be tapped off or the pumping to the extraction column can be ceased prior to pumping the turpentine.

According to a embodiment, the water content of the methanol to be washed is 10 to 40 wt. %. This corresponds approximately to a density of to 0.82 to 0.89 at 25° C.

According to an embodiment, the density of methanol to be washed is 0.85 to 0.87 at 25° C.

According to an alternative embodiment, the water content of the methanol to be washed is 40 to 65 wt. %. This corresponds approximately to a density of to 0.880 to 0.926 at 25° C. According to an embodiment, the density of methanol to be washed is 0.880 to 0.926 at 25° C.

Higher water content improves the separation between the methanol och the non-polar organic solvent, but requires more energy in distilling the methanol. The degree of dilution is thus a trade off between loss of methanol in the washing step and energy needed in the subsequent distillation step.

The methanol mixture after washing may, in addition to methanol, comprise water, acetone, and/or ethanol. To obtain highly concentrated methanol the content of these compounds may be reduced. The content of acetone present in the methanol after washing with non-polar organic solvent may be reduced via distillation. Further, the water content may be reduced by distilling of methanol. Also the separation of methanol and ethanol, to reduce the ethanol content, may be performed by distillation.

According to an embodiment, the methanol is distilled in three steps:

a first distillation step to remove acetone and other compounds being more volatile than methanol;

a second distillation step to remove water and any remaining contaminants being less volatile than methanol;

a third distillation step to remove any remaining ethanol being slightly less volatile than methanol.

In some embodiments, the first and/or the third distillation are dispensed with. Further, the first and second or second and third distillation may be performed in a dividing wall column, also denoted partition column in the art.

Although normally not necessary, the raw methanol may additionally, at some stage of the process, be treated with an oxidizing agent, typically a peroxide, such as hydrogen peroxide or sodium hypochlorite, to oxidize any remaining sulfur compounds as described by Suokas or Metso.

Figure 1:
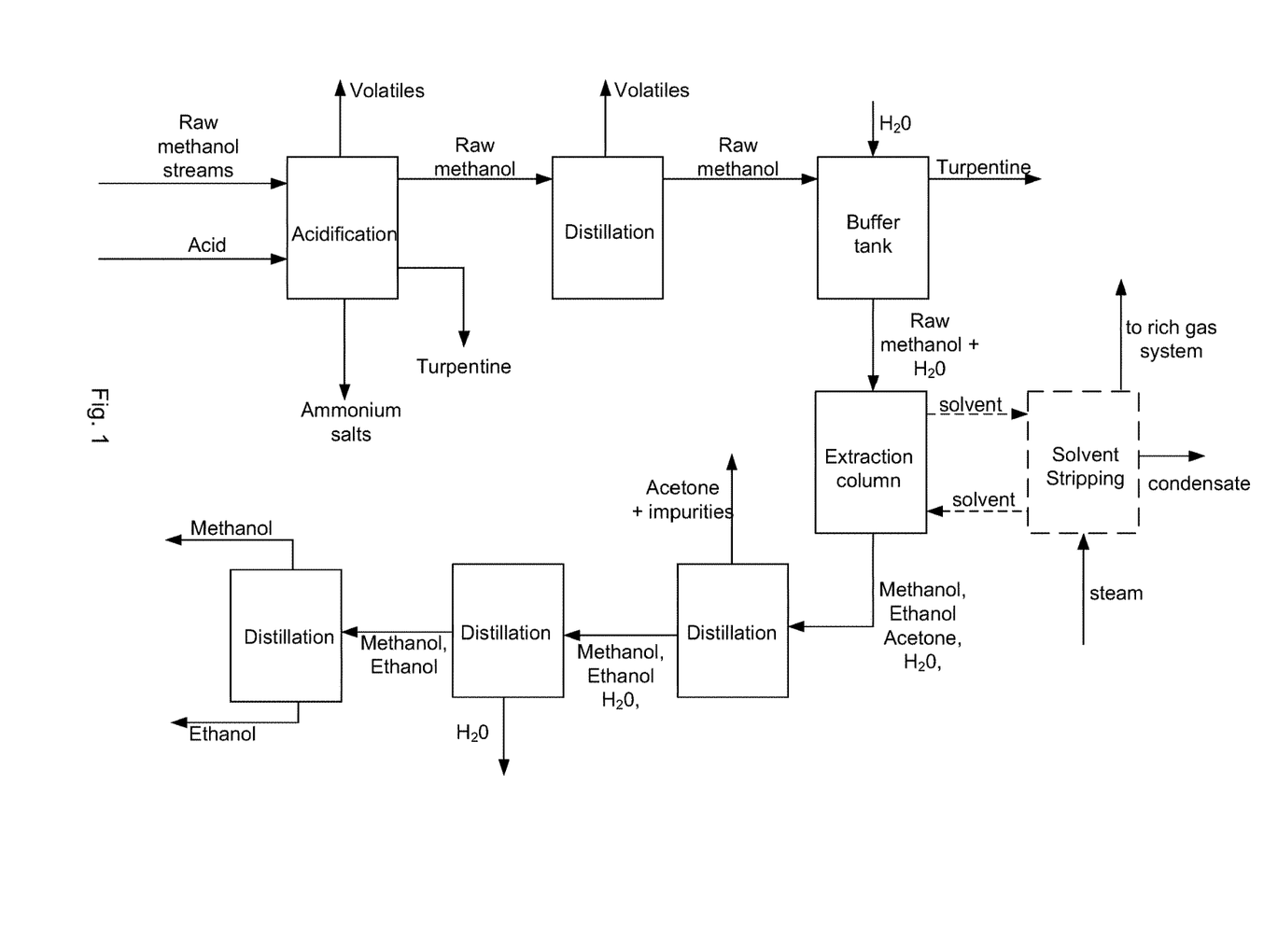
FIG. 1 Depicts an exemplary embodiment for processing raw methanol from a pulping mill according to the present invention.

Based on the above described embodiments, raw methanol from a pulping mill may, may according to an exemplary embodiment as depicted in FIG. 1, be processed in a process comprising the following steps:

acidifying raw methanol comprising sulfurous compounds and nitrogenous compounds;

removing precipitations formed upon acidifying the raw methanol;

optionally removing, e.g. decanting, turpentine;

optionally distilling of sulfurous contaminants;

distilling the acidified methanol from which precipitations have been removed;

diluting the distilled methanol with water;

optionally removing, e.g. decanting, turpentine from the diluted methanol;

washing the diluted methanol with a non-polar organic solvent; and removing acetone, water and/or ethanol by one or several distillation steps.

Various aspects for each step in such exemplary embodiment have been described herein above and are evidently applicable with respect to also to this embodiment. As a non-limiting example, the used non-polar organic solvent is typically re-generated by steam stripping and subsequently re-used in such an exemplary embodiment.

EXPERIMENTAL DATA

Experiments have been performed to compare and determine the performance of raw methanol purification via a non-polar organic solvent.

Example 1

To evaluate whether extraction with a non-polar organic solvent is an industrially viable process simulation of extraction and oil stripping were performed. The simulations were performed in cooperation with the Dep. of Chemical Engineering at Lund University and used simulation software Aspen Plus supplemented with data for vapour-liquid liquid equilibrium (VLLE) (J. & G., 2001). In simulations, hexadecane ($C_{16}H_{34}$) was used as a model substance for the non-polar organic solvent. Hexadecane's vapor-liquid and liquid-liquid equilibrium is well defined which is important for simulation accuracy. Other substances that have been included in the simulations are methanol, dimethyl sulfide, dimethyl disulfide and water.

The simulations clearly show that the extraction of oil should be an industrially viable process. According to the simulation an extraction process with at least 5 steps resulted in a 95% separation of sulfurous compounds.

Example 2

The performance of alternatives methods of extraction of sulfurous compounds from raw methanol was compared. The existing method of Suokas, as described in FI2710, was compared to washing with oil or turpentine and alternative reagents, such as iron chloride. Suokas method was also combined with washing with alternative reagents. The constituents of the raw and the treated methanol were analyzed and the concentrations of methanol in comparison to sulfurous compounds determined.

| Method | Total Sulphur | $H_2S$ (ppm) | $H_4SH$ (ppm) | $(CH_3)_2S$ (ppm) | $(CH_3)_2S_2$ (ppm) | $(CH_3)_2S_3$ (ppm) | $CH_3OH$ (% w/w) |
|---|---|---|---|---|---|---|---|
| Raw methanol (Baseline) | 74000 | 600 | 6000 | 31000 | 5700 | 1900 | 63 |
| Treatment as per Suokas | 340 | 0 | 0 | 30 | 0 | — | |
| Washing with non-polar organic solvent (triglycerides) | 715 | 0 | 300 | 0 | 20 | — | |
| Treatment with turpentine | 552 | 0 | 0 | 0 | 60 | — | |
| Treatment with $AlSO_4$ | 785 | 0 | 800 | 0 | 20 | — | |
| Treatment with $FeCl_2$ | 602 | 0 | 0 | 0 | 20 | — | |
| Washing with non-polar organic solvent + Suokas | 149 | 0 | 0 | 0 | 70 | — | |
| $AlSO_4$ + Suokas | 390 | 0 | 0 | 0 | 109 | — | |
| $FeCl_2$ + Suokas | 187 | 0 | 0 | 0 | 70 | — | |
| $FeSO_4$ + Suokas | 320 | 0 | 0 | 0 | 36 | — | |
| $FeCl_3$ + Suokas | 190 | 0 | 0 | 0 | 523 | — | |
| Fuller's earth + Suokas | 90 | 0 | 0 | 0 | 35 | — | |
| Water + Suokas | 598 | 0 | 0 | 0 | 40 | — | |

The above table shows that extraction with a non-polar organic solvent, such as oil, is a promising method of reducing sulfur compounds in raw methanol. Whilst other methods were capable of reducing the sulfur concentration the reagents in the process are significantly more costly and create waste management issues.

Example 3

In order to experimentally verify the findings in example 1, raw methanol (diluted with 15 wt. % water) was washed with hexadecane (in a weight ratio of 1:1) multiple times to determine the effectiveness of a multi-cycle extraction process with an organic solvent. The experiment comprised of repeatedly washing raw methanol with fresh hexadecane.

The sulfur content of both the methanol and the organic solvent (hexadecane) was measured after every washing step.

| Extraction step | Total sulfur in methanol (ppm) | Total sulfur in solvent (ppm) |
|---|---|---|
| Step 0 (prior to extraction) | 2929 | 0 |
| Step 1 | 842 | 1842 |
| Step 2 | 393 | 470 |
| Step 3 | 223 | 140 |
| Step 4 | 157 | 44 |
| Step 5 | 126 | 17 |
| Step 6 | 114 | 8 |
| Step 7 | 108 | 5 |
| Step 8 | 104 | 3 |
| Step 9 | 102 | 3 |
| Step 10 | 100 | 2 |

This experiment showed that a multi-cycle extraction process with an organic solvent will remove sulfur from raw methanol and confirmed a removal efficiency of >95% over 5 extractions. The sulfur content of the solvent confirms that the sulfur was extracted into the solvent from the raw methanol.

Example 4

After extraction, oil is purified from sulfur compounds by stripping. The potential of the organic solvent to be regenerated was also verified experimentally.

Mineral oil was mixed with raw methanol in a 1:1 weight ratio and mixed for 1 h at 40° C. The two phases were separated from each other and the oil passed through a column filled with glass filler bodies corresponding to less than 1 theoretical plate. A steam flow was forced in a direction opposite to the direction of the oil where the ratio of steam to oil was approximately 4:1. The process of mixing the oil with raw methanol, and subsequently passing the oil and steam through the column was repeated 7 times with the same oil but a new aliquot raw methanol. The sulfur content was measured according to EN ISO 20846.

The results showed that the amount of sulfur remaining in the oil increased with each step. The increase in sulfur content with each step indicates that some of the sulfur reacted with the oil and was bound irreversibly. However, the oil maintained its ability to extract sulfur from the raw methanol despite the increasing sulfur content.

Further, also in the pilot plant runs described below, the sulfur content initially increased in the regenerated oil, but thereafter remained constant. Even after many washing cycles, the oil maintained a good ability for dissolving sulfurous compounds.

| Test | Methanol sulfur content post extraction (ppm) | Oil treatment method | Oil Sulfur content post treatment (ppm) |
|---|---|---|---|
| 0 (raw methanol) | 5694 | — | — |
| 1 | 2611 | No treatment | 3362 |
|  |  | Steam stripping | 80.9 |
| 2 | 2751 | No treatment | 3205 |
|  |  | Steam stripping | 154 |
| 3 | 2700 | No treatment | 3530 |
|  |  | Steam stripping | 246 |
| 4 | 2920 | No treatment | 3622 |
|  |  | Steam stripping | 286 |
| 5 | 2967 | No treatment | 3750 |
|  |  | Steam stripping | 231 |
| 6 | 2882 | No treatment | 2877 |
|  |  | Steam stripping | 317 |
| 7 | 2916 | No treatment | 3746 |
|  |  | Steam stripping | 409 |

Example 5

The components remaining in methanol after alternate processes according to the invention were compared.

Raw methanol was treated by washing with an organic solvent, which was subsequently cleaned with steam stripping 10 times. The sulfur content was reduced to around 100 mg/kg after only 4 to 5 washes. Further washing steps resulted in only minor reductions in sulfur content.

An additional distillation step was also added after the washing with organic solvent. The distillation step further reduced the sulfur content from 140-150 mg/kg to less than 10 mg/kg.

To determine whether an increased purification could be achieved an alkali and peroxide were added to the processed methanol as per Suokas method.

| Process | Compound | Testing protocol | Value | Unit |
|---|---|---|---|---|
| washing with non-polar organic solvent. | Sulfur | EN ISO 20846 | 106 | mg/kg |
| washing with non-polar organic solvent + distillation | Sulfur | EN ISO 20846 | 0.8 | mg/kg |
| washing with non-polar organic solvent + NaOH & H2O2 + distillation | Ethanol | GC-FID | 1.5 | % (m/m) |
|  | Methanol |  | 96.7 | % (m/m) |
|  | Acetone |  | 0.7 | % (m/m) |
|  | Water | EN ISO 12937 | 1.2 | % (m/m) |
|  | Ammonia | DIN 38406-5 mod | <5 | mg/L |
|  | Sulfur | EN ISO 20846 | 1.5 | mg/kg |

The above experiment shows that washing with an organic solvent is an effective method to reduce the sulfur content of methanol. There was no significant difference in the concentration of sulfur when an oxidation step according to Suokas method was performed after the extraction with a non-polar organic solvent.

The results also showed that the methanol contains acetone. This is not negative as the subsequent process using the methanol could be an esterification process for the manufacturing of a methyl ester of rapeseed.

Example 6

In order to verify the lab scale testing a pilot plant was established. The raw methanol (870 $dm^3$) was first treated with sulfuric acid ($H_2SO_4$) and optionally water to remove nitrogenous compounds. Ammonium salts formed upon lowering the pH and were filtered away.

The mixture of raw methanol, acid and water was then heated via a steam fed heat exchanger in a packed column. A condenser at the outlet of the distillation system was enabled after the temperature of the vapor reached 65° C. in order to firstly separate volatile sulfurous compounds. Once the temperature in the pot reached 90° C. the distillation was terminated (residue 112 $dm^3$)

Raw methanol was collected in a buffer tank and diluted with water such that it had a density of around 890 kg/$m^3$. The mixture (758 $dm^3$; 675 $dm^3$ MeOH) was agitated during dilution with compressed air. The mixture was then left to stand overnight and a layer of turpentine separated above the methanol. Increasing the water content lead to separation of turpentine, which previously had been dissolved in the methanol, as a second liquid phase.

Raw methanol was then fed from the buffer tank to the extraction system. The flow of methanol was controlled to ensure that it was ceased before turpentine entered the extraction column. The extraction column comprised 32 perforated plates and was first warmed via a water filled casing. Subsequently the extraction system was filled with the non-polar organic solvent, White Mineral Oil having a density of 15 cSt at 40° C. The non-polar organic solvent could overflow into a steam stripping vessel. Methanol was pumped into the extraction column at a frequency of 50 Hz (equivalent to 116 liters/hour) and the non-polar organic solvent was pumped in at a frequency of 60 Hz (equivalent to 140 liters/hour). The methanol to non-polar organic solvent ratio was around 1 to 1.2.

In the pilot process steam was fed to the stripping vessel to strip the non-polar organic solvent of sulfur. The non-polar organic solvent was regenerated through steam stripping at a ratio of 0.9 kg per kg of 100% methanol or with respect to steam to non-polar organic solvent 0.45 kg steam per kg non-polar organic solvent.

The washed methanol (737 $dm^3$; 652 $dm^3$ MeOH) was manually drained from the extraction column from between the bottom of the column and the first perforated plate. The average sulfur content was 167 mg/kg, corresponding to a sulfur reduction of nearly 94% in the washing step, in line with what to be expected. The loss of the non-polar organic solvent was less than 0.4 wt. % calculated from 100% methanol, thus only a minor make up is deemed to be necessary. Further, no difference in the sulfur content of the extracted methanol was seen over time, confirming that steam regeneration of the solvent is sufficient.

The washed methanol was drained to a distillation column in which the washed methanol was warmed via a steam heat exchanger. The distillation column was provided with a condenser set to 55° C. The first distillates generated are generally acetone and any remaining sulfurous compounds, these were captured for analysis. The set temperature of the condenser was then raised to approximately 57° C. and once again the distillate was captured for analysis. Then the condenser was set to 60° C. and the methanol was condensed and captured for analysis.

The methanol was analyzed at different points throughout the pilot process:

| | |
|---|---|
| Methanol content of mixture prior to dilution with water: | 91% w/w |
| Methanol content of mixture after dilution with water: | 62% w/w |

Figure 2:
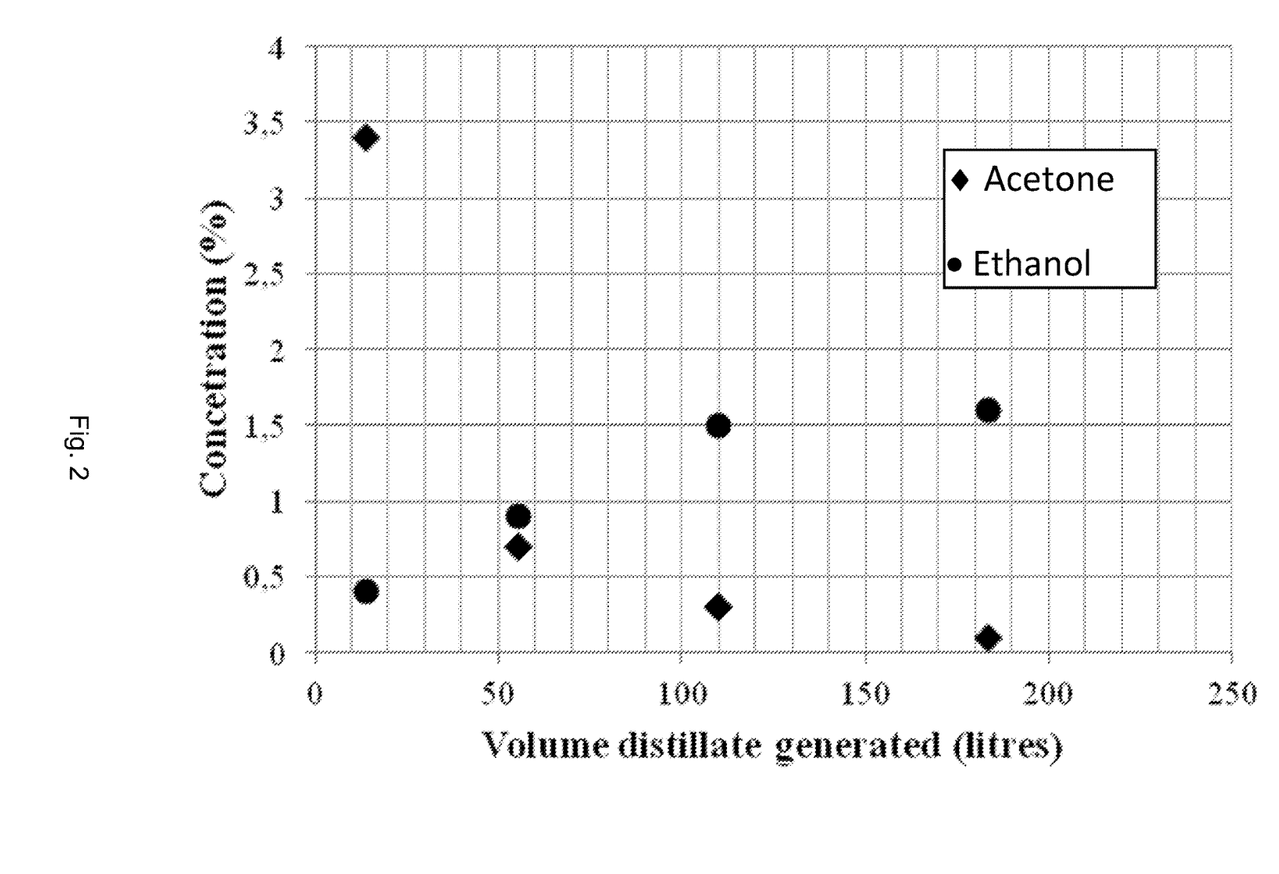
FIG. 2 Depicts the acetone and ethanol content in the distillate after washing raw methanol with a non-polar organic solvent in a pilot plant.

FIG. 2 shows the acetone and ethanol contents of distillate in % w/w on the Y axis with respect to the total volume of distillate generated in liters on the X axis. As can be seen in FIG. 2 the volatile acetone was reduced rapidly and only present at a concentration of 0.1% w/w in the distillate after approximately 180 liters of distillate had been generated.

Figure 3:
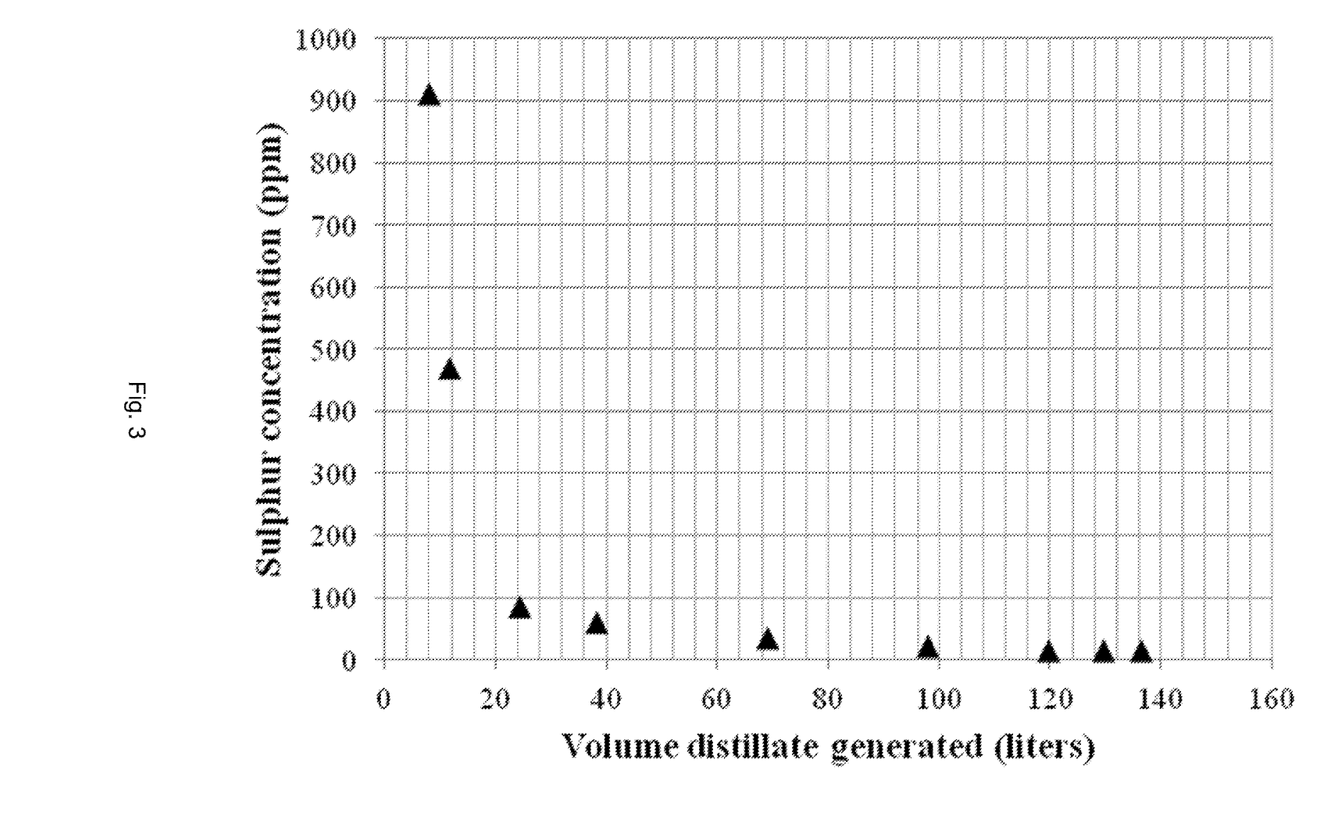
FIG. 3 Depicts the sulfur content in the distillate after washing raw methanol with a non-polar organic solvent in a pilot plant.

FIG. 3 shows the sulfur contents of distillate in ppm on the Y axis with respect to the total volume of distillate generated in liters on the X axis. As can be seen in Figure Y the main components of the sulfur remaining appears to be volatile sulfur, which was distilled away after only 20 liters of distillate had been generated, or non-volatile sulfur remaining in the pot. The sulfur concentration of the distillate after 100 liters was quite stable at approximately 14 ppm. A sulfur content at this level is acceptable for down stream use of the methanol.

The invention claimed is:

1. A method for purifying a composition comprising methanol and sulfurous compounds obtained as a by-product in a Kraft or sulfate process of pulp production in a pulp mill, the method comprises a step of:
    washing the composition comprising methanol and sulfurous compounds with a non-polar organic solvent to extract sulfurous compounds, wherein the non-polar organic solvent is a solvent comprising at least 60 wt. % alkanes and/or cyclo-alkanes having a carbon number of 14 or higher, and/or wherein the non-polar organic solvent comprises at least 10 wt. % triglycerides which are liquid at temperatures of less than 40° C.;
    wherein the non-polar organic solvent has a boiling point higher than 100° C. but lower than 600° C. and a viscosity at 40° C. of not more than 100 cSt.

2. The method according to claim 1, wherein the non-polar organic solvent comprises less than 2.5 wt. % polycyclic aromatic hydrocarbons.

3. The method according to claim 1, wherein the non-polar organic solvent is a mixture of hydrocarbons.

4. The method according to claim 3, wherein the non-polar organic solvent is selected from the group consisting of white mineral oil, mineral oil, and mixtures thereof.

5. The method according to claim 1, wherein the density at 25° C. of the non-polar organic solvent is in the range 0.80 to 0.90 g/cm$^3$; or wherein the density at 25° C. of the non-polar organic solvent is in the range 0.91 to 1.20 g/cm$^3$.

6. The method according to claim 1, wherein the method further comprises a step of diluting the composition comprising methanol and sulfurous compounds with water before being washed with the non-polar organic solvent, the methanol content in the composition comprising methanol and sulfurous compounds before being diluted being at least 65 wt. %, wherein the water content of the diluted aqueous composition comprising methanol and sulfurous compounds and the non-polar organic solvent are selected such that their difference in density at 25° C. is at least 0.01 g/ml.

7. The method according to claim 6, wherein the diluted aqueous methanol phase has higher density than the non-polar organic solvent.

8. The method according to claim 6, further comprising a step of separating turpentine before washing the diluted aqueous methanol.

9. The method according to claim 1, wherein the methanol to non-polar organic solvent volume ratio is 1:0.75 to 1:5.

10. The method according to claim 1, wherein the washing is performed at a temperature of 15 to 60° C.

11. The method according to claim 1, wherein the non-polar organic solvent is regenerated by steam stripping, and re-used as non-polar organic solvent in the washing step.

12. The method according to claim 1, wherein the composition comprising methanol and sulfurous compounds is acidified and precipitated salts are removed before washing the composition comprising methanol and sulfurous compounds with a non-polar organic solvent, and wherein the method further comprises a step of separating turpentine after the composition comprising methanol and sulfurous compounds has been acidified.

13. The method according to claim 12, further comprising a step of distilling the methanol subsequently to having been acidified, wherein the distillation is performed in a manner such that volatile sulfurous compounds firstly are distilled off and then methanol.

14. The method according to claim 12, wherein the amount of hydrogen sulfide, methyl mercaptan, and dimethyl sulfide, being more volatile than methanol, are reduced by distillation prior to acidifying the methanol.

15. The method according to claim 1, wherein the process further comprises a step of separating hydrogen sulfide and methyl mercaptan prior to the washing step.

16. The method according to claim 1, wherein the content of water, acetone, and ethanol in the washed methanol is reduced by distillation in three steps after the wash with the non-polar organic solvent.

17. A method of purifying raw methanol from a Kraft or sulfate process of pulp production in a pulp mill, the raw methanol comprising sulfurous compounds and nitrogenous compounds, the method comprising steps of:
    acidifying the raw methanol to form precipitations;
    removing the precipitations;
    optionally at least partly removing turpentine;
    optionally distilling sulfurous contaminants;
    distilling the acidified methanol from which precipitations have been removed to obtain distilled methanol composition;
    diluting the distilled methanol composition with water to obtain a diluted methanol composition;
    optionally removing turpentine from the diluted methanol composition;
    washing the diluted methanol composition with a non-polar organic solvent to extract sulfurous compounds, wherein the non-polar organic solvent is a solvent comprising at least 60 wt. % alkanes and/or cyclo-alkanes having a carbon number of 14 or higher, and/or wherein the non-polar organic solvent comprises at least 10 wt. % triglycerides which are liquid at temperatures of less than 40° C., wherein the non-polar organic solvent has a boiling point higher than 100° C. but lower than 600° C. and a viscosity at 40° C. of not more than 100 cSt; and
    removing acetone, water and/or ethanol by one or several distillation steps.

18. The method according to claim 17, further comprising a step of re-generating non-polar organic solvent by steam stripping and subsequently re-using the re-generated nonpolar organic solvent in washing the diluted methanol composition.

\* \* \* \* \*